US006944536B2

(12) United States Patent
Singleton

(10) Patent No.: US 6,944,536 B2
(45) Date of Patent: Sep. 13, 2005

(54) METHOD AND SYSTEM FOR IDENTIFYING MEDICAL FACILITIES ALONG A TRAVEL ROUTE

(75) Inventor: Timothy Singleton, Tempe, AZ (US)

(73) Assignee: MedAire, Inc., Phoenix, AZ (US)

( * ) Notice: Subject to any disclaimer, the term of this patent is extended or adjusted under 35 U.S.C. 154(b) by 313 days.

(21) Appl. No.: 10/066,058

(22) Filed: Feb. 1, 2002

(65) Prior Publication Data

US 2004/0204837 A1 Oct. 14, 2004

(51) Int. Cl.[7] .............................................. G01C 21/30
(52) U.S. Cl. ................................. 701/209; 340/995.19
(58) Field of Search .............................. 701/201, 202, 701/209, 211, 213, 214, 23, 25; 340/988; 342/357.01, 357.06, 357.08, 357.13

(56) References Cited

U.S. PATENT DOCUMENTS 6,157,891 A * 12/2000 Lin ............................. 701/301
6,208,934 B1 * 3/2001 Bechtolsheim et al. ..... 701/209
6,278,938 B1 * 8/2001 Alumbaugh ................. 701/208

* cited by examiner

*Primary Examiner*—Yonel Beaulieu
(74) *Attorney, Agent, or Firm*—David E. Rogers; Squire, Sanders & Dempsey L.L.P.

(57) ABSTRACT

A system and method for identifying medical facilities along a travel route preferably includes an input device, a processor, Microsoft SQL server database and a memory storing various information regarding medical facilities. For on-demand determination of medical facilities along a travel route, the input device preferably includes a GPS receiver providing the current geographical coordinates of a patient requiring medical assistance to the processor. The processor compares the geographical coordinates of the patient to coordinates of medical facilities in the database to determine medical facilities near the patient. A user of the system may also input a type of medical emergency, preferred language and insurance information to refine the search for medical facilities. The processor may also calculate a projected travel route using navigational software. The identified medical facilities may be displayed to a user in any manner and/or saved in a navigational computer for reference in case of a medical emergency.

59 Claims, 9 Drawing Sheets

| Name | Geographical Coordinates | Country | Languages | City/Address | Tel. No. | Number of Beds | ER Operation Hrs. | Medical Services |
|---|---|---|---|---|---|---|---|---|
| St Anns Medical Center | N 33 26.05 W 112 0.48 | Dominican Republic | English; Spanish; Portuguese | 1342 Med Way Bianca 00412 | ##### | 28 | 24/7 | General ER/Cardiology Specialist |
| St. Anthony Regional Medical Center | N 69 51.64 W 80 13.97 | United States | English; Spanish | 555 Ash Street Hays, Ks. 67601 | ##### | 342 | 24/7 | General ER/Cancer Research Center |
| Stuart Hadley Cancer Clinic | N 88 20.06 W 90 58.27 | Canada | French; English | 19 E. Adams Alberta, ON 00231 | ##### | 55 | 8a.m.-9p.m.EST. | MRI/Radiology only |
| Suinercht Emergency Center | N 79 46.02 E 30 21.34 | Germany | German; English | 11 Stutgard Ave. Munich GM 77890 | ##### | ##### | 24/7 | |
| Swaarthout Cardiology | N 71 23.09 W 91 34.54 | United States | English | ##### | ###### | | N/A | |
| Sweeney Lutheran Hospital | N 68 45.22 W 85 23.31 | United States | English German | ##### | ##### | | | |
| ~~~~~~~ | | | | | | | | |

FIG. 8

METHOD AND SYSTEM FOR IDENTIFYING MEDICAL FACILITIES ALONG A TRAVEL ROUTE

FIELD OF THE INVENTION

The invention relates to a method of identifying medical facilities along a travel route or identifying medical facilities on demand while a person in need of medical treatment is away from his/her domicile.

BACKGROUND

The need for immediate medical treatment, hereinafter called a medical emergency, sometimes arises during travel or when a person is otherwise away from his or her domicile. For example, a person traveling on an airplane between New York and Los Angeles may experience a medical emergency such as a heart attack, stroke, or other injury.

As used herein, a person in transit or away from his/her domicile that experiences a medical emergency is referred to as a "patient," and includes, but is not limited to (1) passengers, crew members, and anyone traveling, regardless of the mode of transportation, which may be vehicles such as airplanes, boats, trains, buses and automobiles, and (2) any person away from his/her domicile. "Domicile" means a person's permanent residence. "Medical facility" means any medical care provider, and includes hospitals, clinics, doctor's offices, emergency medical technician ("EMT") services and ambulance services. "Suitable stopping points" means stopping points, such as airports, ports, bus stations and train stations, suitable for accommodating a vehicle on which a patient is resident, if the patient is in a vehicle. For example, if the patient is on a plane, a suitable stopping point is an airport with the proper size and facilities to accommodate a landing.

When a medical emergency arises while a patient is aboard a vehicle, a patient may sometimes be treated while on the vehicle, for example, by a crew member or passenger, until the vehicle reaches its ultimate destination. In some cases, however, a patient cannot wait to reach the ultimate destination (e.g., Los Angeles) to visit a medical facility. It is therefore desirable for the patient (or someone else on board the vehicle, such as a crew member) to be able to quickly identify (1) the location of one or more medical facilities near the vehicle or otherwise along the travel route, and/or (2) contact information related to such medical facilities.

Medaire, Inc., of Phoenix, Ariz. provides a MedLink® emergency medical service that, among other things, identifies one or more qualified medical facilities near a specific point on a travel route. MedLink® services are provided to common carriers, such as commercial airlines; to private aircraft; to military and private maritime vessels; and to corporate travelers who may be traveling by various modes of transportation anywhere throughout the world. To provide MedLink® services, a database of medical facilities is created, maintained and updated. The database preferably includes for each medical facility in the database: (1) the location (e.g., address), (2) contact information, including the phone number, (3) the type of medical services provided, (4) a quality rating for the facility based on services provided, and (5) languages spoken at the facility. Following is an example of the use of this MedLink® service.

A passenger on a commercial flight suffers a concussion midway between Belize and Tokyo. To obtain medical assistance for this medical emergency, a flight crew member contacts Medaire, Inc., thereby accessing MedAire's MedLink® service. The MedAire personnel contacted by the flight crew member is called a "communications specialist." Once notified of the medical emergency, the communications specialist determines if the medical emergency requires consultation with a physician. This initial determination is sometimes referred to as triaging. If the medical emergency requires consultation with a physician, the communications specialist contacts an emergency room physician. The physician may then direct either the flight crew or passengers in treating the patient.

Depending on the severity of the medical emergency, the physician may recommend that the patient be immediately transported to a medical facility. In that case, the communications specialist determines the location of the airplane by asking a crew member, accesses MedAire's database of medical facilities, which includes at least the location of each medical facility, and assists the flight crew in identifying a suitable medical facility to handle the medical emergency. This identification is made based upon one or more of the following factors (1) the location of the airplane, (2) the respective location of each of the medical facilities in the database, (3) the locations of airports at which the plane can land, (4) the nature of the medical emergency (e.g., the type of injury or sickness), (5) the types of services offered by each of the medical facilities (e.g., preferred medical facilities are those equipped, either with appropriate personnel and/or medical devices, to handle that particular type of medical emergency). The flight crew or communications specialist then contacts the airport designated for the unscheduled landing, and may contact the medical facility or facilities identified to handle the medical emergency.

A flowchart showing the method described above for determining a qualified medical facility is illustrated in FIG. 1. The method generally includes identifying one or more medical facilities 10, which includes at least obtaining the location and preferably the contact information for each. Once one or more medical facilities are identified, the medical specialties each offers are preferably identified (in order to determine the suitability of each for handling different types of emergencies), and each medical specialty it offers are reviewed 11. The facilities are evaluated by obtaining information related to each medical facility's personnel and medical equipment, preferably by someone from MedAire, Inc. contacting the medical facility (either in person and/or by fax and/or by phone) and asking questions to obtain such information. Information related to each medical facility is stored in a database 12 for retrieval when needed.

As shown in step 13 of FIG. 1, a person, such as a crew member aboard a plane, contacts a communications specialist requesting the location of a medical facility, and provides the current location of the patient and the nature of the medical emergency. Using the current location of the patient and the nature of the medical emergency, the communications specialist retrieves the names, locations and other relevant information in the database related to one or more of the medical facilities 14 and provides this information to the crew member 15. The crew member and/or the communications specialist then identifies, using one or more of the criteria previously discussed, a suitable medical facility to handle the medical emergency.

While this method is effective, it requires verbal communications between a person who is usually in an aircraft or other vehicle and a communications specialist. Because wireless communications are subject to interference, such as interference caused by noise, weather, or electromagnetic interference (EMI) of other devices, these communications may be impossible to initiate or may be interrupted. Accordingly, it would be advantageous to identify one or more medical facilities along a travel path without the necessity of real-time verbal communications.

SUMMARY OF THE INVENTION

The present invention addresses this problem and others by providing a method for identifying one or more medical facilities along a travel path. One method, according to the invention, preferably includes the steps of (1) comparing a calculated travel route to medical facility information maintained in a database, and (2) determining one or more medical facilities capable of handling medical emergencies on or near the travel route based upon the comparison. Optionally, the method may also include the step of calculating a travel route between a starting point and a destination point and/or generating an output, such as a written report of medical facilities along a travel route, prior to travel.

Another method, according to the invention, identifies one or more medical facilities on demand and preferably includes the steps of (1) determining a location of a patient, who may be in a vehicle in transit, (2) comparing the location of the patient with locations of medical facilities maintained in a database, (3) identifying at least one medical facility based on the comparison, and (4) displaying the identified medical facility/facilities to a user. This method electronically identifies and retrieves information related to at least one medical facility, including at least its location, and relays the information to a user (such as a crew member aboard an aircraft) in either visual or audio format without verbal communications with a communications specialist.

Either of the above methods could include additional steps, such as: (1) providing for one or more of the identified medical facilities in the database; (2) storing, retrieving and including in the output: the medical specialties offered, a quality rating for one or more of the medical specialties offered, directions to the medical facility, information related to the method of payment (such as types of insurance) accepted, and the languages spoken; and (3) identifying one or more suitable stopping points, if applicable, near the medical facility.

BRIEF DESCRIPTION OF THE DRAWING

Further aspects and advantages of the invention will become apparent from the following description in reference to the appended drawing wherein like references denote like elements and wherein:

FIG. 8 illustrates an example portion of a medical facility database.

DETAILED DESCRIPTION OF THE PREFERRED EMBODIMENTS

Figure 2:
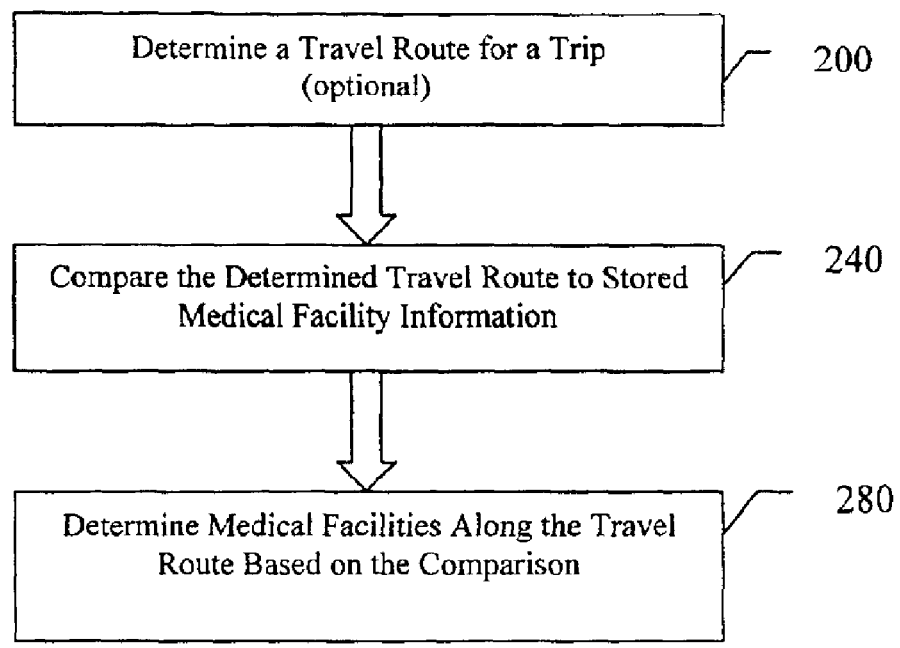
FIG. 2 is a flow diagram illustrating a method of identifying the location of a medical facility along a travel route according to one preferred embodiment of the invention.

Turning now to the drawing for the purpose of describing a preferred embodiment of the invention and not to limit same, FIG. 2 shows a method of determining one or more medical facilities along a travel route, the method preferably including the steps of: (1) (optional) calculating 200 a travel route for a trip; (2) comparing 240 the calculated travel route to information relating to medical facilities, which information is maintained in a database, and (3) identifying medical 280 facilities near or on the travel route based on the comparison. The identified medical facilities are formatted in any output such that they may be communicated to a user. For example, they may be formatted in a written report, printed list, or displayed on a screen, or stored electronically such as on a tape or on disk for visual or audio retrieval at a later time (such as during a flight). Determining 200 the travel route, is optional as the travel route may instead be supplied.

The stored medical facility information includes at least the name and location (e.g., physical address) of each medical facility. The stored information may also include for one or more of the medical facilities one or more of the following: (1) contact information (e.g., phone number, fax number and/or names of contact personnel), (2) the location of suitable stopping points, such as airports, train stations or ports, (3) one or more medical specialties provided, (4) quality ratings derived for one or more of the medical specialties provided, (5) languages spoken, (6) payment methods (such as types of insurances) accepted, (7) directions to the facility, and (8) the proximity of each medical facility to one or more suitable stopping points. The information relating to medical facilities is compiled and stored in a memory, database, printed report, book or other storage medium.

The identification includes at least a comparison of the travel route to the locations of respective medical facilities in the database but may also be based in part upon one or more of the following factors: (1) the travel route; (2) the mode of transportation utilized, (3) depending upon the mode of transportation utilized, the location of suitable stopping points (if applicable), (4) available transportation from suitable stopping points (if applicable) to suitable medical facilities, (5) the medical specialties available at a particular medical facility, and (6) the relevant quality rating of a particular medical facility or quality rating of its relevant medical specialties. When one or more of the above factors are considered, one or more medical facilities are identified (for example, two hospitals, or a hospital and ambulance service may be identified). These identified medical facilities are then included in an output. In the event of a medical emergency, a user of the output selects one or more suitable medical facilities (such as a hospital and an ambulance service to transport the patient to the hospital) from the identified medical facilities based upon the location of the patient at the time the selection is made. Other factors may also be considered in selecting a suitable medical facility, such as the nature of the medical emergency.

The locations of suitable stopping points could be stored in the database or included as part of the travel route. A method according to the invention therefore could also identify the location of suitable stopping points and include such information in the output. In that case, the estimated travel time from suitable stopping points to one or more identified medical facilities, or directions from suitable stopping points to one or more identified medical facilities, could be included as part of the output. For a mode of transportation such as an automobile, that does not require a suitable stopping point, this factor would not be considered.

The selected medical facility(ies) may not be the one(s) closest to the patient at the time of the selection. For example, if the patient is aboard an airplane and there is no airport capable of accommodating a landing near the medical facility closest to the airplane at the time of the selection, that medical facility would not be suitable. Consequently, selecting a suitable medical facility from the identified medical facilities requires either judgment by a person, or calculation by an electronic processor, or both, of one or more of the factors identified above at the time the selection is made. For example, a medical facility having a cardiology unit and accepting Blue Cross Blue Shield® (BC/BS) medical insurance may be selected from the identified medical facilities, when, for example, a person in transit having BC/BS insurance suffers a heart attack, and can safely wait to reach this particular medical facility.

Figure 3:
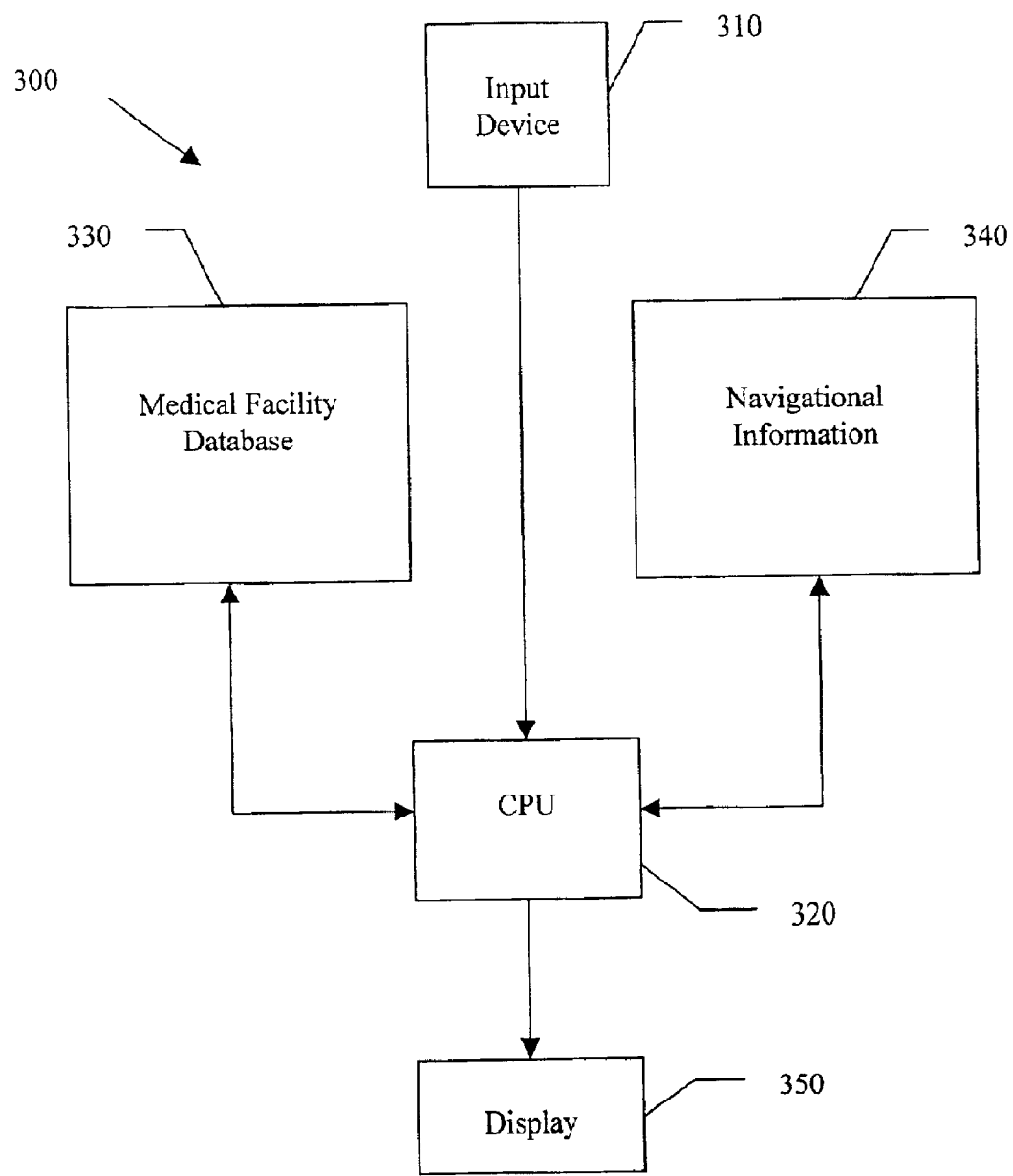
FIG. 3 is a block diagram of a system for determining medical facilities according to a preferred embodiment of the invention.

Turning now to FIG. 3, a preferred system 300 for practicing the method of FIG. 2 is shown. System 300 may be implemented in any manner utilizing any device or devices suitable for practicing a method according to the invention. For example, it may be implemented in any type of computer or computer system, locally in any existing processing device such as a cellular phone, a personal digital assistant (PDA), a laptop or handheld computer, or a car, plane or other type of vehicle having a suitable device, such as a navigation computer.

System 300 includes an input device 310 and a processing unit, or CPU, 320. Input device 310 enables a user to enter various information into processing unit 320 of system 300, and may be any apparatus(es) or system(s) or combinations thereof resident at any location or locations, capable of performing this function. Input device 310 may be a microphone, mouse keyboard, touch screen or other device facilitating user input. Input device 310 may also be a combination of any of the aforementioned devices and a location identification device to provide processing unit 320 location information to assist in the identification of a medical facility and (optionally) identify a suitable stopping point. Preferably, input device 310 is a keyboard and/or a disk reader. Input device 310 may be integrated with display 350 using, for example, a graphic user interface (GUI).

In the preferred embodiment, CPU 320 identifies medical facilities on or near the travel route. It may also identify, and may also retrieve and include as part of the output, other information from the database, such as the location of each suitable stopping point, or any stored information relevant to the medical facilities. Any or all of the identified information may be included as part of the output. Processing unit 320 may be any device, or combination of devices, capable of processing the information from input device 310 and comparing the input information with at least some information in database 330 to identify and generate an output of one or more medical facilities along a travel route. Processing unit 320 may accomplish this task in any one of a variety of ways, depending on the type of information received from input device 310. Unit 320 may reside at any location and, if unit 320 is a system or more than one device, the individual components of the system, or the various devices, may reside at different locations, in which case they may communicate with each other via either wired or wireless connections.

Medical facility database 330 is any memory, storage medium, system, device or combination thereof that can store information related to medical facilities. For example, database 330 may be a printed list that is manually created and updated. Preferably, database 330 is electronically maintained for ease of updating and searching. Medical facility database 330 is preferably Microsoft SQL server database. Database 330 may be resident at any location or locations, including a land-based computer or electronic device, a computer or electronic device on board a vehicle (such as a computer on board an aircraft), a handheld electronic device. Database 330 need not be at the same location as either processing unit 320 or input device 310. Medical facility database 330 includes information pertaining to medical facilities, which is entered into database 330 by any suitable method or device, including by input device 310. The information regarding each of the medical facilities may include, but is not limited to, one or more of the following: (1) name and location, (2) contact information, such as phone number, fax number and contact personnel, (3) its relative location to suitable stopping points and/or transportation infrastructure (e.g., airports, highways, bus stations, train stations and ports), (4) directions to the facility, (5) types of medical services offered, (6) the identity of staff members and the associated specialties/background of each, (7) an overall quality rating, (8) a quality rating for each medical specialty offered, (9) payment options available including accepted insurance providers, and (10) languages spoken by employees or staff members. Medical facility database 330 only need include the name and location of each medical facility.

Since the information in database 330 may be updated, and the updates may occur frequently (e.g., change of medical personnel, quality rating, equipment acquisitions related to the facility's ability to handle medical emergencies), medical facility database 330 may be updated in any suitable manner, including by inputting additional or new information into database 330 utilizing input device 310. Alternatively, a radio frequency ("RF") data link (e.g., through input device 310) or any other device, wired or wireless, for facilitating the exchange of information, may be used to load additional or new information into database 330. In this manner, medical facilities may be identified using the most accurate and updated information available in the database. By way of example, an aircraft may download into its onboard computer information pertaining to a flight prior to its departure, including updated weather, flight hazards and additional Air Traffic Control (ATC) information. This downloaded information could possibly also include updates to medical facility database 330 or download the entire medical facility database before each trip. The information downloads could also be provided by a satellite link before or during transit.

Calculating the travel route may be performed using any procedure for determining a navigational course including using a hand-held map, a website on the Internet, or by any processing means having access to geographical information. Additionally, the travel route might also be provided. For example, the pilot of an airplane may obtain a flight plan (i.e., the airplane's travel route) from an air traffic control facility and transmit or input it to processing unit 320 for comparison to information in database 330. If included as part of a method according to the invention, the calculation of a travel route may be performed in any manner including (1) manually plotting a route between two points on a map, or (2) calculating a travel route using navigational software. If the travel route is calculated by a method and system according to the invention, it is preferably calculated using navigational software, which is preferably first loaded in or otherwise interfaced with a processing unit, such as unit 320. A user would preferably input the starting point and destination point of travel, using any suitable device(s) or method (s), such as input device 310. The inputted starting point and destination point may include longitude and latitude coordinates, names of cities, physical street addresses and/or other information that identifies points of reference, respectively.

In a preferred embodiment of utilizing mapping software to calculate a travel route, processor 320 receives latitude and longitude coordinates for the starting point and destination point from input device 310. Processor 320 then determines the travel route between the starting point and destination point by utilization of mapping software 340 stored in a memory. In a preferred embodiment, mapping software 340 is FliteStar™ and FliteMap® software available from Jeppesen (a Boeing Company). Information pertaining to this software is located at http://www.jeppesen.com. Mapping software 340 determines a route of travel between the starting and destination point. Optionally, it identifies points of reference along the travel route (e.g., airports, landmarks, cities). Software 340 may generate a separate output consisting of a travel route including the starting and destination points, and optionally displays other information, such as suitable stopping points (such as airports) near the suggested travel route.

If the travel route is provided by another entity it may, for example, be downloaded into processor 320 via input device 310, or in some other manner. Processor 320 then compares the determined travel route with medical facility database 330.

Once processor 320 identifies medical facilities corresponding to a travel route the located medical facilities may be formatted in any output capable of ultimately transmitting information to a user. The output may be any device, structure or apparatus capable of communicating the names and locations of identified medical facilities, including a storage mechanism or system for storing information related to the identified medical facilities in, for example, electronic media, such as disk, tape or hard drive, for later audio or visual review. For example, the output may be a print out in any format or may be stored electronically for use during a flight, where it could be graphically or textually represented electronically on a display 350. Display 350 may be any type of device for displaying information and may be or include a CRT, LCD, LED display, or a printer for producing a printed document. Additionally, the output may be downloaded or saved into a memory (not shown) for later retrieval.

From this output including identified medical facilities along a travel route, one or more suitable medical facilities are selected in the event of a medical emergency. The selection may be made by a human user, either solely by judgment or with the assistance of software. Alternatively, software could be used to make the selection.

System 300 may also be implemented remotely via a communications system such as interfacing with the Internet. For example, for creating a flight plan including medical facilities along the travel route, a pilot may use a personal computer (PC) or other electronic device to log onto a website. The pilot may enter a starting point and destination point based on prompts from the website. The server hosting the website, or another processing device accessible by the website, may act as processor 320 and access mapping software 340 and medical facility database 330 to generate and provide the pilot with a flight plan reflecting medical facilities. Alternatively, the flight plan may be generated by another source, such as a computer on board the aircraft, and be communicated through the server to the medical facility database to generate a flight plan with medical facilities. The generated flight plan with corresponding medical facility information may be stored on-board and displayed on an aircraft display and/or may be printed on an on-board printer.

Another embodiment of the present invention is directed to identifying a medical facility on-demand. On-demand means that a patient suffering a medical emergency can access CPU 320 via input device 310. In this embodiment, input device 310 may be used to input the location of a patient. Device 310 may include, or may be, an identification device such as a global positioning system (GPS) receiver, and may be aboard any type of vehicle, such as an automobile, plane, bus, boat or train. Input device 310 provides current geographic position information of a patient to processor 320; it may do so continuously or when a user instructs it to do so by inputting appropriate commands and/or information. Input device 310 may also be utilized to input other information such as one or more of the following: (1) the type of medical emergency, (2) the name of the patient, (3) the medical history of the patient, and (4) the type of vehicle on which the patient is traveling.

The identification of a suitable medical facility is based upon a comparison of one or more of the same factors previously described and includes at least a comparison of the location of the patient and the locations of medical facilities within database 330. Processor 320 compares the location of the patient (which is usually the location of the vehicle in which the patient is traveling) to information stored in the medical facility database 330 to determine, for example, the nearest suitable medical facility. In this embodiment, system 300 may not include mapping software 340 or any device or system for calculating a travel route, since medical facilities are determined on demand rather than being identified based on a predetermined travel route. However, mapping software 340, or other software or another device or method may be utilized to provide directions to an identified medical facility.

For on-demand medical facility identification, input device 310 may be used to input additional information from a user to processor 320 to more accurately identify a suitable medical facility, and optionally, also identify a suitable stopping point (if applicable). For example, in the case of air travel, a user may input the nature of the medical emergency and the location of one or more suitable airports for receiving the airplane. The method and system according to the invention could then locate one or more medical facilities based upon the information. The pilot (or another member of the flight crew), or an automated software routine, may then identify one or more suitable medical facilities, and optionally, a corresponding airport in order to minimize overall travel time to a suitable medical facility.

Processor 320 may be configured to further allow the user to inquire about additional information about medical facilities maintained in database 330 through input device 310. Alternatively, such information may automatically be located and retrieved when information is requested about medical facilities along a travel route. Output generated by user inquiries may be displayed on display 350 and may include this additional information. For example, a user may input via device 310 a specific type of medical emergency (e.g., heart attack, birthing) into processor 320. Processor 320 would search medical facility database 330 not only for medical facilities along the travel route, but for medical facilities equipped to handle the type of medical emergency inputted by the user. Processor 320 could then display relevant information about the medical facilities and (optionally) suitable stopping points on display 350, which could be viewed by the user.

Figure 1:
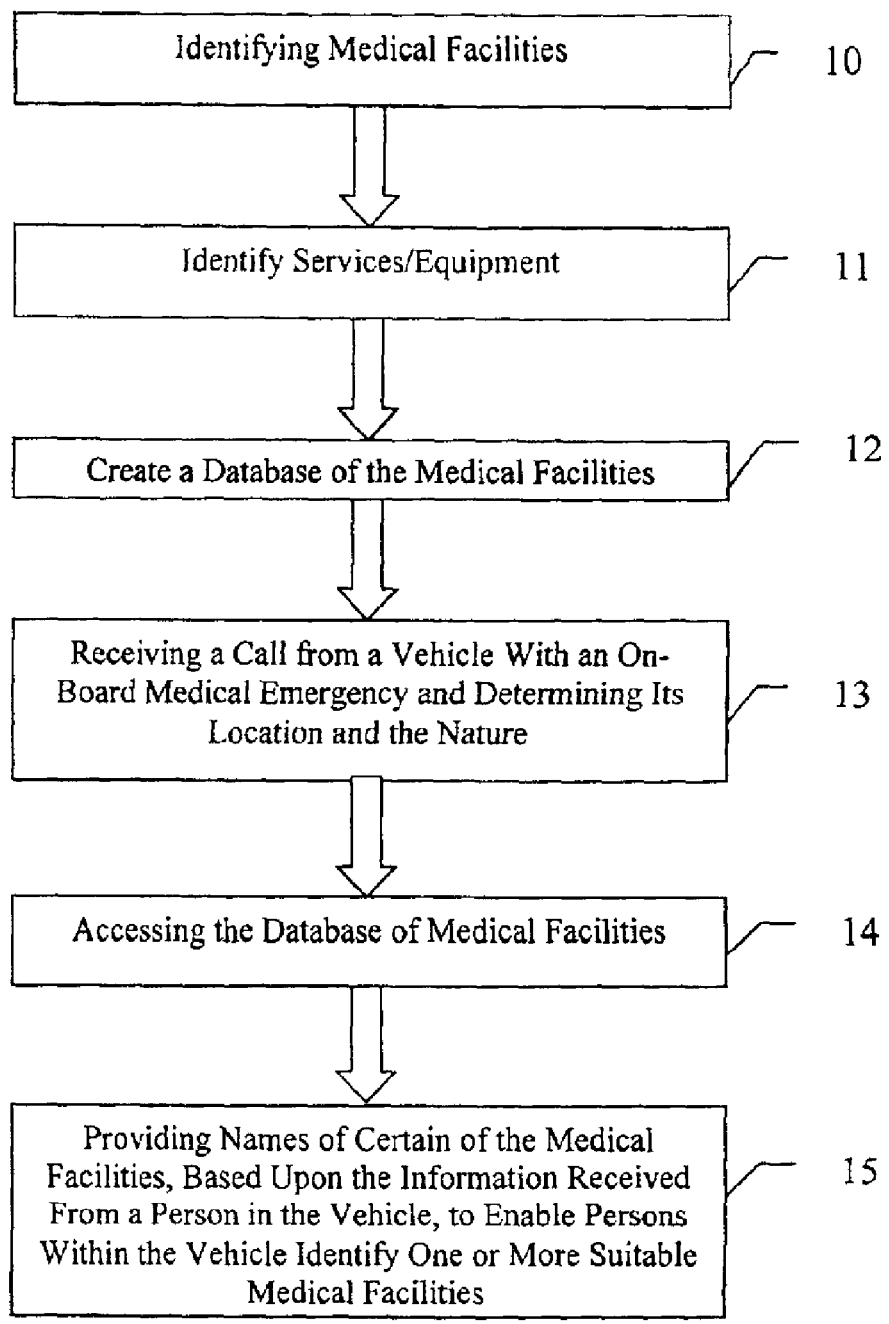
FIG. 1 is a flow diagram illustrating a method of the related art.

When implementing the systems and on-demand methods of the invention it may be desirable (for example, if the user is in an automobile) to provide directions to a user for proceeding to the identified medical facility. Accordingly, processor 320 shown in FIG. 1, may be configured to process the current geographic position of a patient with that of an identified medical facility to provide directions to guide a user to the identified medical facility. The methods and systems of the present invention may be adapted to provide this capability, for example, by using or integrating navigational software such as the Fugawi Complete Navigation System (GPS required) available at http://fugawi.com.

Figure 4:
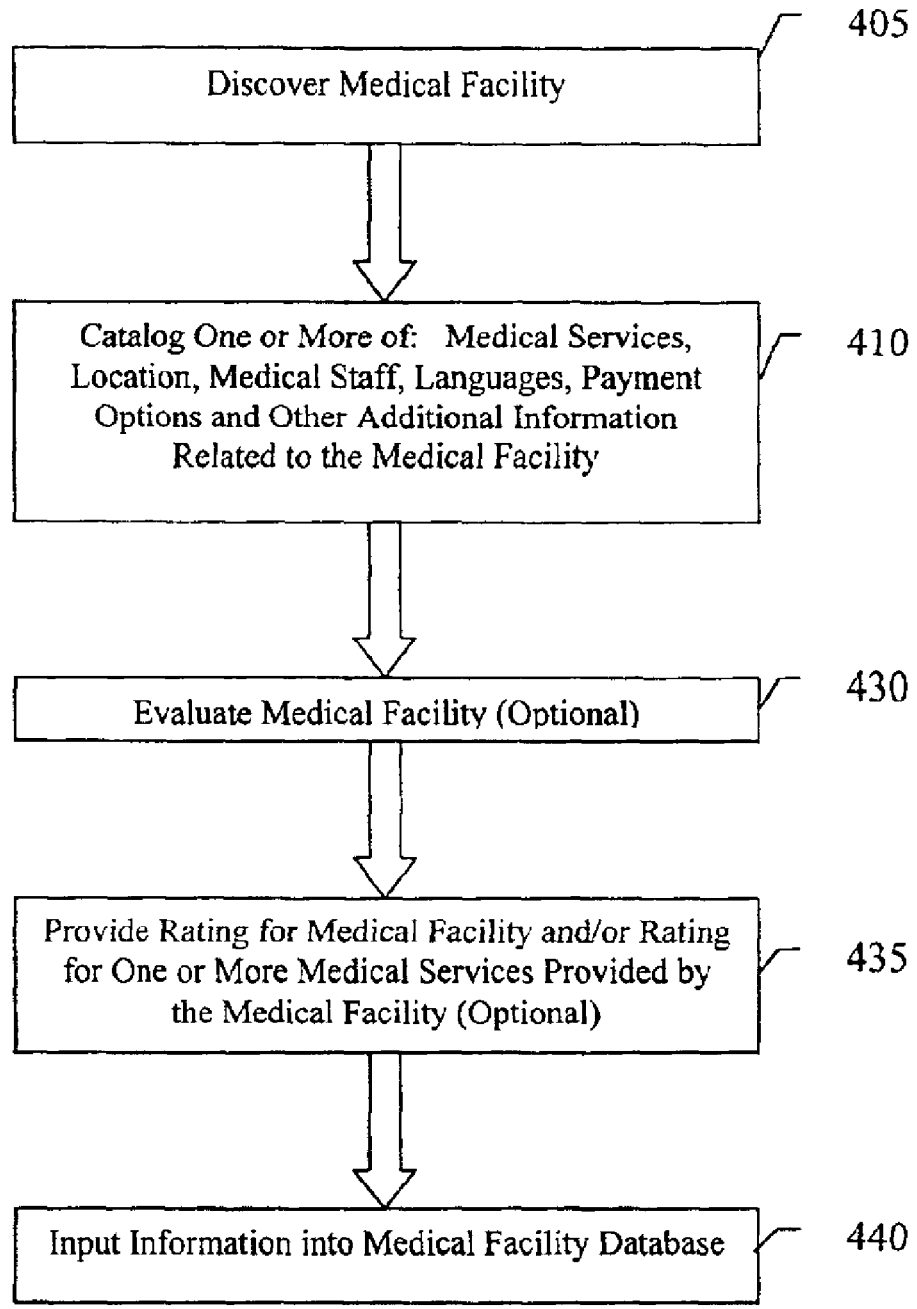
FIG. 4 is a flow diagram illustrating a method of compiling/updating a medical facility database.

A method 400 of obtaining and updating medical facility database 330 will now be described with reference to FIG. 4. For each medical facility in the database, one or more of the following steps are performed:

One or more medical facilities is first located or otherwise identified 405. The medical facility is then typically contacted, such as by phone, fax or by physical visitation to obtain, update, and/or verify information related to the medical facility. Optionally, the location of each medical facility relative to transportation infrastructures may also be cataloged 415.

One or more of the following items are preferably identified, reviewed and/or cataloged for each identified medical facility: (i) location, preferably including one or more subcategories of street addresses, cities, states, countries, regions, geographical (such as GPS) coordinates and positional relation of one or more landmarks (such as hotels or public buildings) in the area, and/or relative suitable stopping points; (ii) types of medical services (e.g., the available medical services are identified and cataloged to enable matching a medical emergency with medical facilities capable of handling it. For example, if a medical facility has a magnetic resonance imaging machine (MRI), or radiological equipment, that medical facility can be cataloged to provide medical services requiring such equipment, e.g., services relating to fractures or internal scans.); (iii) medical staff and languages spoken (the names, background and languages of doctors and medical staff including respective practice areas may be catalogued to assist in evaluating and identifying a medical facility, for example, by matching specialties and languages to a given medical emergency; (iv) payment options (possibly including types of insurances accepted); and (v) any additional information including hours of operation, medical insurance options, costs, on call-status, telephone number, number of facility beds, etc., is cataloged in database 330 as well that may assist in evaluating, locating or selecting a medical facility.

A physical inspection of one or more medical facilities may also be performed to verify and/or evaluate general criteria such as the cleanliness, hours of operation, nurse and general staffing support and other factors related to the quality of the medical facility. Based on the forgoing information, each medical facility may optionally be evaluated 430 and assigned a quality rating 435 to assist a user of system 300 to choose a medical facility. Collected information is preferably entered into database 440 and made available to system 300.

Figure 5:
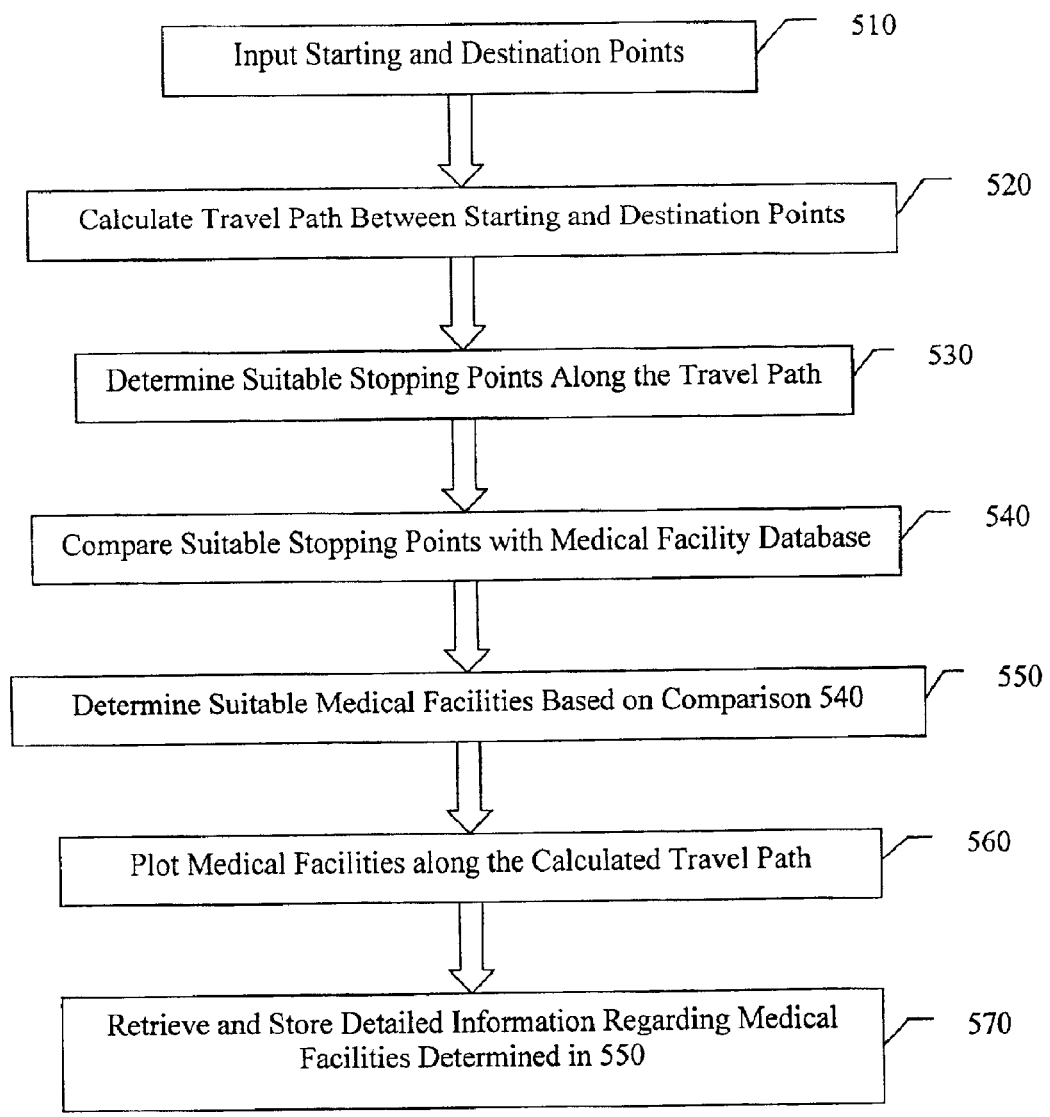
FIG. 5 is a flow diagram representing a method for finding a medical facility according to a preferred embodiment of the invention.

Turning now to FIG. 5, in this optional embodiment of the invention, suitable stopping points may be determined along a projected travel route and compared with medical facility information to identify medical facilities along the travel route. In a preferred method, either calculates a travel path by inputting information, e.g., starting and destination points 510 using system 300 and calculating a travel path 520 with suitable stopping points along the travel path 530. The suitable stopping points may then be compared with locations of medical facilities stored in the medical facility database 540 to identify medical facilities within a selected distance of the suitable stopping points 550. If the suitable stopping points along a travel route are determined, they can be (1) stored for identification when a medical emergency arises during transit; (2) plotted on a map (printed or electronic) along with the projected travel route 560 for reference; (3) transmitted to a vehicle in transit requesting emergency medical information (note: this may be accomplished without steps 510–530, but rather by providing heading and/or current positional information of the vehicle in transit to determine a suitable stopping point for comparison.); or (4) used via any combination of the above options (1)–(3). Once one or more medical facilities are identified 550, additional information about the medical facilities may optionally be provided or displayed to a user (e.g. any of the types of information discussed in respect to FIG. 4.

Figure 6:
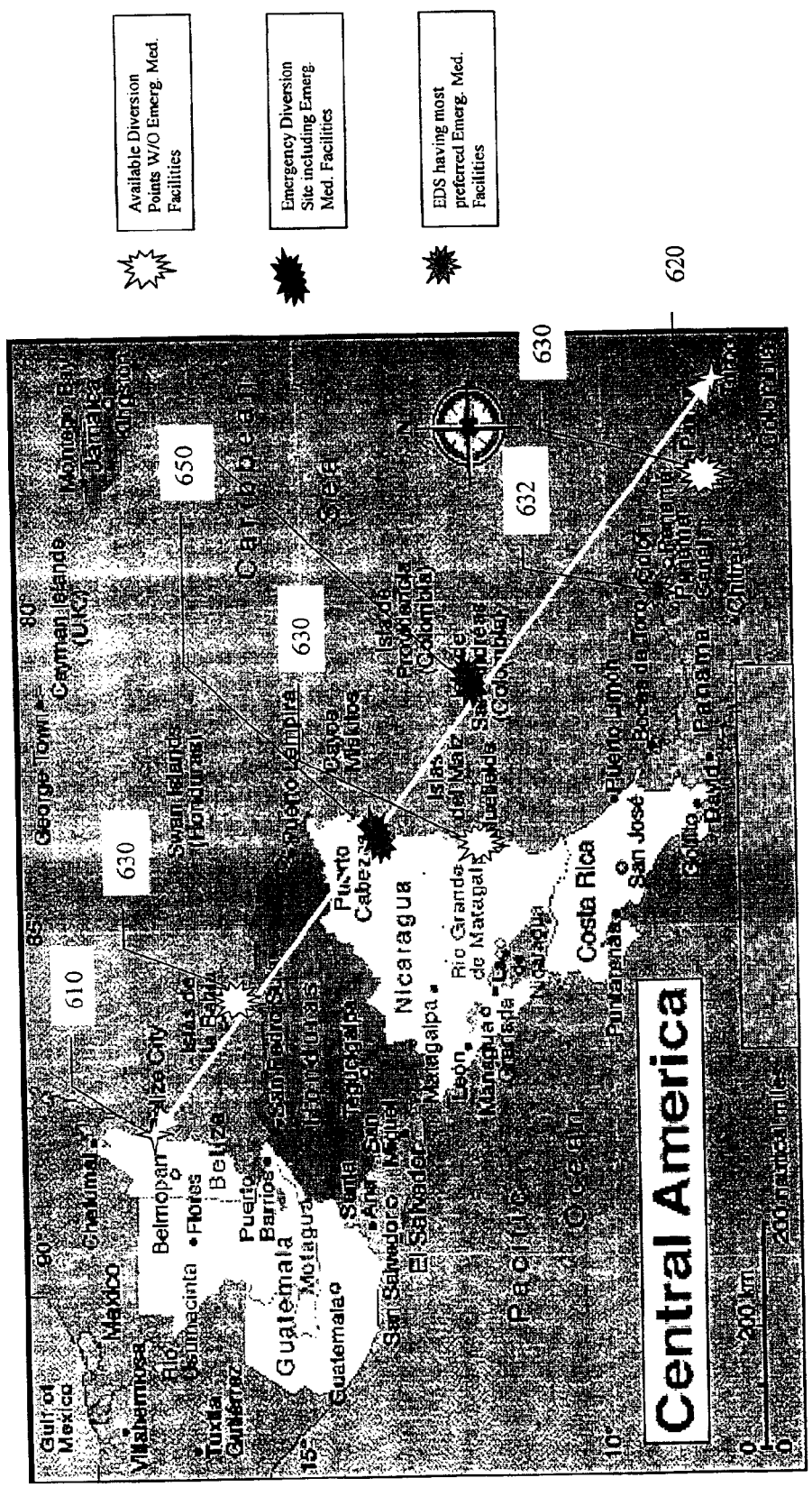
FIG. 6 illustrates an example of determining medical facilities along a travel path.

FIG. 6 illustrates an example method for identifying medical facilities along a travel route. A pilot of a private airplane is planning to travel between Belize City, Belize (e.g., starting point 610) to Turbo, Columbia (i.e., destination point 620). Suitable stopping points 630, 632 and 650 having landing strips large enough to facilitate the private airplane are identified within a 200 km range of the travel route between the starting point 610 and destination point 620. The locations of the determined suitable stopping points are compared with a medical facility database containing information regarding medical facilities in the region of the stopping points. In this example, the comparison determines that suitable stopping points 630 and 632 having appropriate medical facilities within five miles of each exist along the travel route between Belize City and Turbo. The medical facility database also identified Colon, Panama as a suitable stopping point 632 having the most preferred medical facility based on criteria related to the medical emergency and location of the patient. If the patient is in a plane, the pilot may print a map indicating the suitable stopping points and suitable medical facilities. In addition or alternatively, the pilot may store the navigational information including suitable stopping points and medical facilities in a flight computer for retrieval during the flight should a medical emergency occur. Additional information regarding the determined medical facilities may be downloaded prior to the flight and/or retrieved during the flight in the case of a medical emergency.

Figure 7:
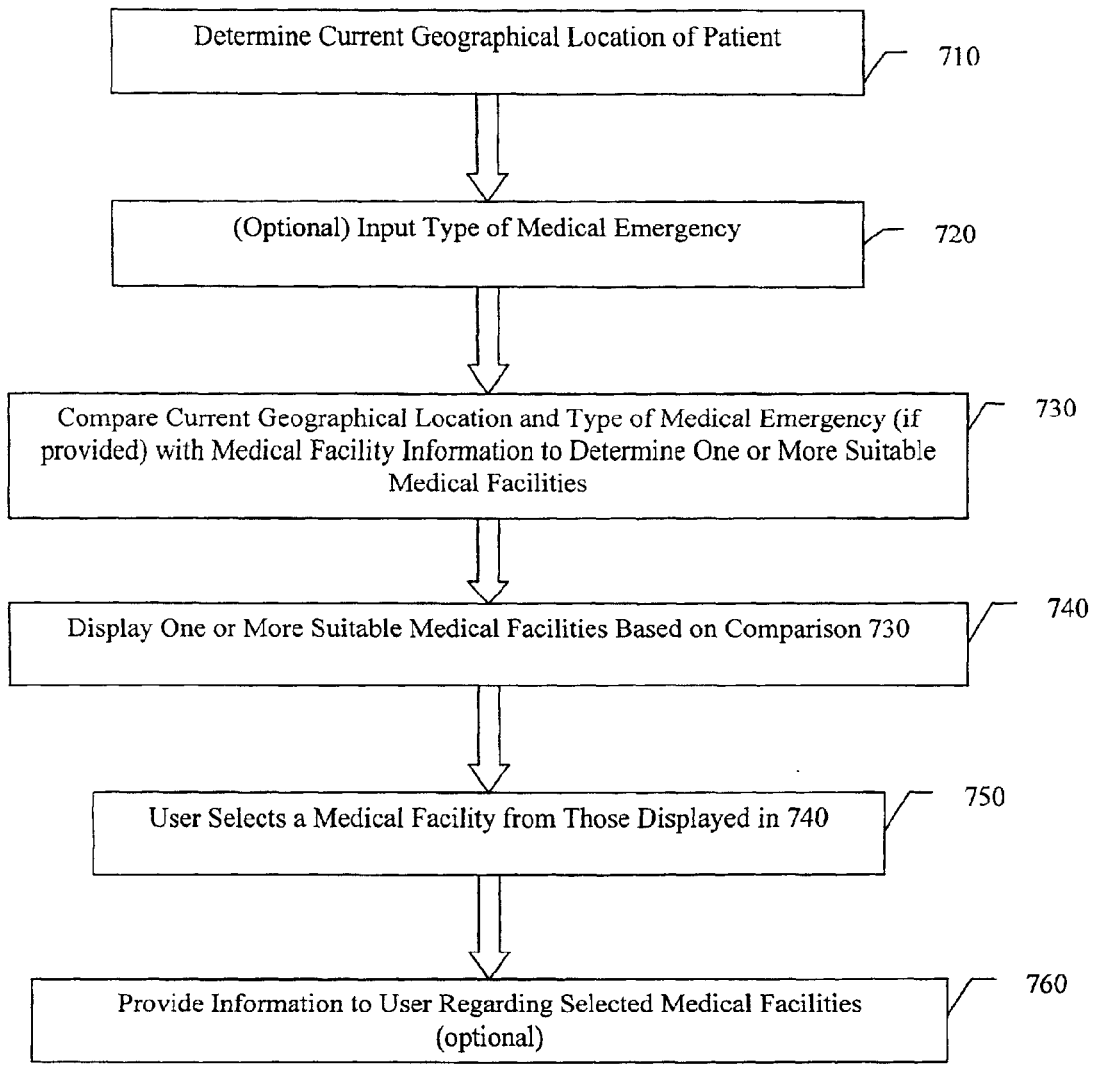
FIG. 7 illustrates a method for determining medical facilities according to a second preferred embodiment of the invention.

FIG. 7 illustrates a process 700 for determining a suitable medical facility on demand. In this case, suitable medical facilities are determined after the occurrence of a medical emergency while in transit. When a medical emergency arises, the current geographical location of the patient in transit is determined 710. The patient's location may be determined by a GPS receiver located on board the vehicle, by noting a current transit position on a map (e.g., mile markers, nearest city), communication with a tracking authority (e.g., ATC) or from a vehicle navigational computer tracking transit position by speed and time of departure, etc.

In addition, to further assist in the selection of the medical facility from the identified medical facility, a user may optionally input the type of medical emergency occurring 720, if that information is known. The current geographical location of the patient is compared to a database of one or more medical facilities to identify one or more suitable medical facilities 730. The suitable medical facilities are displayed or otherwise conveyed to a user based on the comparison 740. Suitable medical facilities may be displayed or made known to a user by highlighting, displaying in different colors or assigning numerals to the displayed medical facilities to denote preferred and most preferred suitable medical facilities.

A user may optionally then select a desired medical facility from the displayed suitable medical facilities 750 based on the user's preference and/or display recommendations. The selection may occur by touching the desired displayed suitable medical facility using a GUI or by entering a reference designation into a keypad or any other manner for selecting a preference. Once selected, further information may be provided to the user 760 regarding the selected medical facility including contact information, directions and additional detailed information for the medical facility of the type previously discussed. Based on this information, the user may contact and/or proceed to the selected medical facility or return to the display of suitable medical facilities to obtain detailed information for different medical facilities.

FIG. 8 is an example table illustrating a portion of medical facility information that may be contained in a database. Preferably, geographical coordinates 810 are stored for each medical facility listed in the database. Additional information as previously described may be included in the database for each medical facility including the country 820 and city address 830 of each medical facility location.

Figure 9:
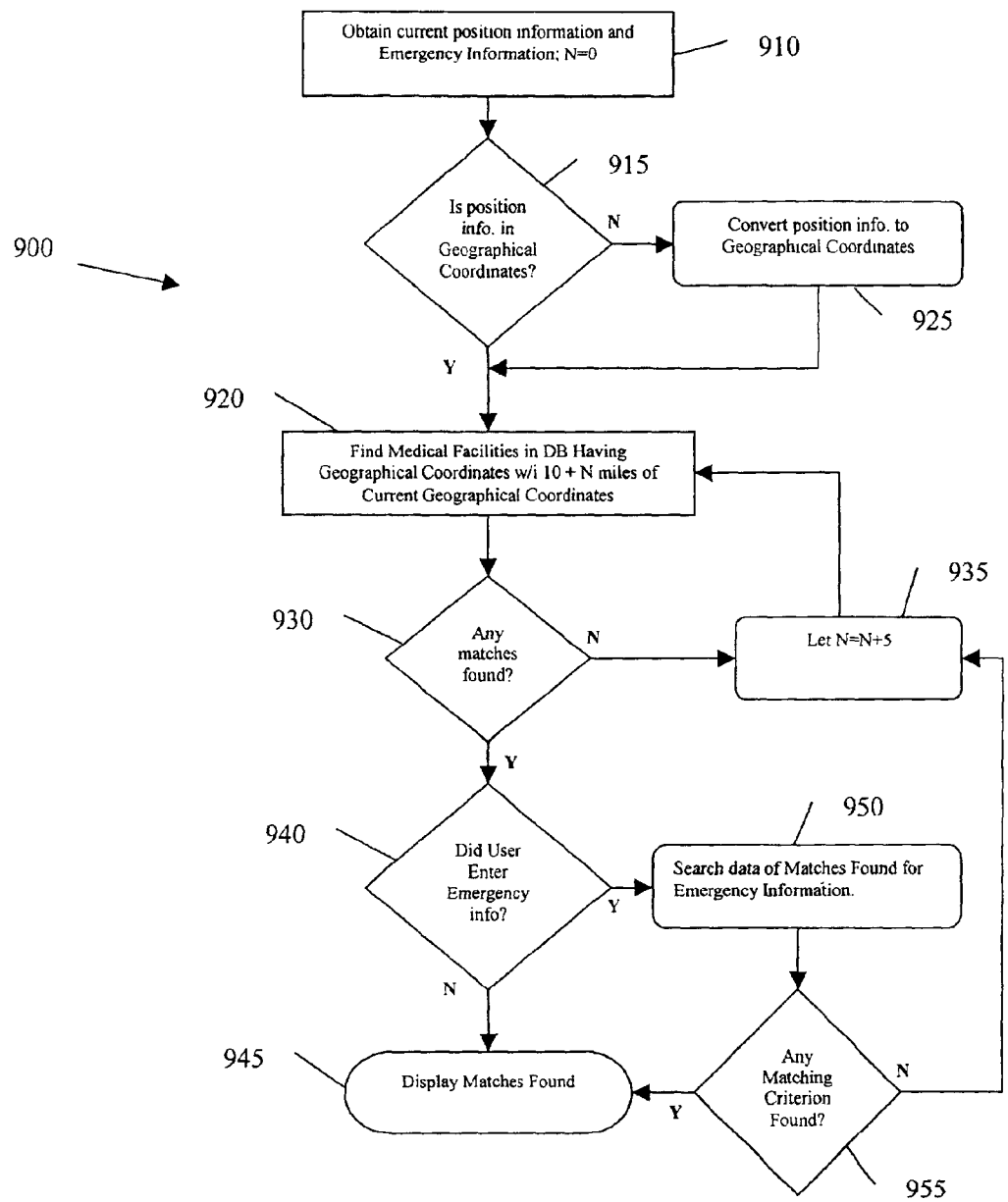
FIG. 9 illustrates a preferred method for finding and displaying potential medical facilities.

FIG. 9 is a flow chart outlining a comparison method 900 for identifying medical facilities. Preferably, the current location of a patient is obtained (via entry by a user, GPS or other input) 910, and the user may have the option of inputting the nature of the medical emergency to identify a suitable medical facility. Information inputted may include a language spoken by the injured party, type of insurance, type of medical emergency, as well as any information relevant for choosing a suitable medical facility such as the type of information previously discussed. Next, the current location of the patient is preferably identified, for example, in latitudinal and longitudinal coordinates 915, or converted into coordinates 925, in order to perform a search for a suitable medical facility. This type of conversion is known and thus is not explained in further detail here.

Once the current position of the patient is identified, the medical facility database is searched for medical facilities within a particular range of the patient's position 920. Key indexing, Boolean field searching or other known database searching techniques may be used for searching the database and the particular range selected may vary depending on the mode of transportation as well as the type medical emergency. For example, an airplane traveling at 500 mph may have, depending upon the location of suitable stopping points, a large number of suitable medical facilities within a relatively short travel period, whereas an automobile on a highway may search for medical facilities within a range of ten miles from its current position. A user may even input a desired geographical range for finding available emergency medical facilities.

After searching the database for medical facilities within the particular range, it is determined whether any suitable medical facilities are identified 930. If not, the range is incremented 935 and the search is performed again 920 repetitively until at least one suitable medical facility is identified. If a suitable medical facility is found, it is determined whether the user inputted any information related to the medical emergency to assist is locating a suitable medical facility 940. If not, the identified medical facility(ies) are displayed to the user 945. If emergency information was provided, the information fields associated with each facility identified are searched for matching criteria 950. For example, if a user inputted the language "Spanish" as part of the emergency information 910, the data fields of each medical facility identified 920 are searched for this criterion. If a medical facility having matching criterion is found 955, it is displayed to user 945. In addition, other medical facilities not having matching criterion may also be displayed. If no matching criterion is found, the range of search for medical facilities having matching criterion may be incremented 935 until one having matching criterion is found. Alternatively, the matching criterion may be deleted in order to conduct a less restrictive search.

It should be noted that the foregoing steps for identifying medical facilities reflect only examples and that more features may be added or features removed from the preferred embodiments to accommodate an apparatus or system utilized by a user. For example, a system having a clock may automatically exclude the search 920 from identifying medical facilities that have hours of operation inconsistent with the current time (i.e., the medical facility is closed). Moreover, the method may be performed without any input from a user (except for an initial demand for finding a medical facility).

Unless impossible, the inventor envisions the methods and systems described herein: (i) may be performed in any sequence and/or combination; and (ii) the components may be combined in any manner. Although there have been described preferred embodiments of the invention, variations and modifications are possible and the invention described herein is not limited by the specific disclosure above, but rather is defined by the scope of the appended claims and their legal equivalents.

What is claimed is:

1. A method for identifying the location of medical facilities along a travel route, the method comprising:
    (a) mapping a travel route;
    (b) comparing the travel route with a database of medical facilities, wherein the database includes the name and location of each medical facility maintained therein;
    (c) identifying one or more medical facilities along the travel route based on the comparison; and
    (d) preparing an output of the identified medical facilities along the travel route, the output including a name and address of each of the identified medical facilities.

2. The method of claim 1 wherein the travel route is a flight plan.

3. The method of claim 1 wherein the one or more medical facilities comprises hospitals and ambulance services.

4. The method of claim 1 wherein the one or more medical facilities is a plurality of medical facilities.

5. The method of claim 4 wherein the plurality of medical facilities comprises one or more hospitals and one or more ambulance services.

6. The method of claim 1 wherein the travel route is mapped by a software program.

7. The method of claim 1 wherein the travel route is mapped manually.

8. The method of claim 1 wherein the output is a written report.

9. The method of claim 1 wherein the output is a computer readable file.

10. The method of claim 9 further comprising the step of loading the computer readable file into the on-board computer of an aircraft.

11. The method of claim 1 wherein the output further includes a quality rating for at least one of the one or more medical facilities.

12. The method of claim 11 wherein the quality rating obtained for each medical facility is based in part upon a telephonic interview with one or more personnel of each medical facility to determine each facility's ability to handle one or more types of medical emergencies.

13. The method of claim 1 wherein the database is maintained within an electronic storage device.

14. The method of claim 1 wherein the output further includes a suitable stopping point along a travel route.

15. The method of claim 14 wherein the suitable stopping point is an airport.

16. The method of claim 1 that further comprised the step of selecting from the one or more identified medical facilities a suitable medical facility.

17. The method of claim 1 wherein the database further includes, for at least one of the medical facilities in the database, information selected from the group consisting of:
(a) languages spoken, (b) proximity to suitable stopping points, (c) one or more medical specialties offered, (d) a quality rating for at least one of the medical specialties offered, and (e) payment methods accepted.

18. The method of claim 17 wherein the output further includes, for at least one of the medical facilities in the database, information from the group consisting of: (a) languages spoken, (b) proximity to suitable stopping points, (c) one or more medical specialties offered, (d) a quality rating for at least one of the medical specialties offered, and (e) payment methods accepted.

19. A method for identifying a medical facility to a person in a vehicle moving along a travel route, the method comprising:
(a) providing a database of medical facilities, the database including a name and location for each of the medical facilities;
(b) establishing a non-verbal communications link between the vehicle and the database;
(c) identifying the location of the person;
(d) identifying, based partly on the location of the person and the database of medical facilities, a medical facility; and
(e) communicating the name and location of the identified medical facility to the person via the non-verbal communications link.

20. The method of claim 19 wherein the vehicle is selected from the group consisting of an automobile a plane, a boat, and a train.

21. The method of claim 19 wherein the database of medical facilities includes a phone number for at least some of the medical facilities.

22. The method of claim 19 wherein the person identifies his/her position by inputting it using a keyboard.

23. The method of claim 19 wherein the person identifies his/her position by inputting it using a keypad of a wireless electronic device.

24. The method of claim 19 wherein the database of medical facilities includes a quality rating for one or more of the medical facilities.

25. The method of claim 19 wherein the database of medical facilities includes the types of medical emergencies at least one of the medical facilities is equipped to handle.

26. The method of claim 21 wherein the phone number for the identified medical facility is communicated to the person.

27. A method of identifying medical facilities along a travel route, the method comprising:
(a) comparing the travel route to a database containing medical facility information; and
(b) identifying at least one medical facility on or near the travel route based on the comparison.

28. The method of claim 27 further comprising the step of calculating the travel route.

29. The method of claim 28 wherein the travel route is calculated using software.

30. The method of claim 27 that further includes the step of identifying a suitable stopping point along the travel route.

31. The method of claim 27 wherein the travel route is a flight plan.

32. The method of claim 28 wherein the travel route is a flight plan and the method further includes the step of identifying one or more suitable stopping points, wherein each of the suitable stopping points is an airport.

33. A method of identifying medical facilities along a travel route, the method comprising:
(a) comparing the travel route to a database containing medical facility information;
(b) identifying at least one medical facility on or near the travel route based on the comparison; and
(c) identifying a suitable stopping point along the travel route; wherein the medical facility is determined by one or more of the factors selected from the group consisting of: (a) type of medical services provided by the medical facility, (b) hours of operation of the medical facility, (c) available emergency equipment at the medical facility, (d) payment options available at the medical facility, and (e) cleanliness of the medical facility.

34. The method of claim 27 further comprising the step of displaying the travel route and identified medical facilities on at least one of an electronic screen and a printed document.

35. The method of claim 27 further comprising the step of displaying the identified medical facilities on at least one of an electronic screen and a printed document.

36. The method according to claim 27 further comprising the step of downloading and storing information pertaining to identified medical facilities.

37. A method of identifying medical facilities alone a travel route, the method comprising:
(a) comparing the travel route to a database containing medical facility information;
(b) identifying at least one medical facility on or near the travel route based on the comparison; and
(c) downloading and storing information pertaining to identified medical facilities wherein the downloaded and stored information includes at least one of the following: (a) types of medical services available at each identified medical facility; (b) the hours of operation for each identified medical facility; (c) contact information for each identified medical facility; and (d) languages spoken at each identified medical facility.

38. The method of claim 27 wherein the steps of comparing and identifying are performed by a processing device reading machine-readable code.

39. The method according to claim 28 wherein the steps of comparing, identifying and calculating are performed by a processing device reading machine-readable code.

40. The method according to claim 36 wherein the downloaded and stored information includes a rating of one or more of the identified medical facilities.

41. The method according to claim 40 wherein the rating is based on at least one of the following: (a) an overall quality of the medical facility, and (b) a medical specialty available at the medical facility.

42. A system for determining medical facilities along a travel route of an aircraft, the system comprising:
   (a) an input device for providing aircraft location information;
   (b) a memory storing a database containing information relating to a plurality of medical facilities;
   (c) a processor operative to compare the aircraft location information with the database containing information relating to a plurality of medical facilities and identify at least one medical facility and a corresponding airport along the travel route of the aircraft based on the comparison; and
   (d) a display operative to show the identified at least one medical facility and corresponding airport along the travel route of the aircraft.

43. The system according to claim 42 wherein the provided location information comprises a starting point and a destination point and wherein the memory also stores navigational information for calculating the travel route based on the location information.

44. The system according to claim 42 wherein the input device comprises a global positioning system (GPS) receiver.

45. The system according to claim 42 wherein the display comprises one of an LCD, LED and CRT display.

46. The system according to claim 42 wherein the display comprises a printing device.

47. The system according to claim 42 wherein the input device comprises means for a user to input information relative to determining the at least one medical facility along the travel route.

48. A method of locating a medical facility for an aircraft in transit, the method comprising:
   (a) determining a current location of the aircraft in transit;
   (b) comparing the current location of the aircraft in transit with locations of medical facilities stored in a database;
   (c) identifying at least one medical facility and a corresponding landing location which is near the current location of the aircraft based on the comparison; and
   (d) displaying the corresponding landing location for the at least one medical facility to a user in the aircraft.

49. The method of claim 48 further comprising the step of selecting, by the user, a medical facility from the displayed at least one medical facility.

50. The method of claim 48 further comprising providing navigational instructions for the user to fly the aircraft in transit to the corresponding landing location of the selected medical facility.

51. The method of claim 48 wherein before identifying the at least one medical facility, the method further comprises the step of inputting information relative to a medical emergency in order to assist in identifying the at least one medical facility.

52. The method of claim 51 wherein the inputted information includes for comparing with the database at least one of: a type of medical emergency, a language preference, a type of insurance coverage, and a maximum distance from the current location to a medical facility.

53. A method of identifying medical facilities along a flight route, the method comprising:
   (a) inputting navigational information pertaining to the flight route; and
   (b) combining the navigational information with medical facility information stored in a database, the medical facility information including location and contact information of a plurality of medical facilities.

54. The method of claim 53 wherein each medical facility is a predetermined distance from airports along the flight route.

55. A database containing information related to medical facilities, the database configured to be accessed by a processor processing flight plan software to produce at least one potential emergency diversion site along a flight path.

56. A computer program having machine readable code stored on a tangible medium comprising:
   (a) code for obtaining a travel route;
   (b) code for comparing the travel route with information in a medical facility database;
   (c) code for identifying at least one medical facility based on the comparison; and
   (d) code for generating a display of the at least one identified medical facility.

57. A system for identifying medical facilities along a travel route, the system comprising:
   (a) input means for inputting travel location information;
   (b) storage means for storing a database containing information relating to a plurality of medical facilities;
   (c) processing means for comparing inputted travel location information with the information relating to the plurality of medical facilities stored in said database and for identifying at least one medical facility based on the comparison; and
   (d) display means for displaying information related to the identified at least one medical facility.

58. The system of claim 57 wherein said processing means comprises a website server.

59. The system of claim 57 wherein the information related to the identified at least one medical facility includes directions to the at least one medical facility.

* * * * *